(12) United States Patent
Michot et al.

(10) Patent No.: US 8,697,824 B2
(45) Date of Patent: Apr. 15, 2014

(54) CROSS-LINKABLE BI-SULPHONYL DERIVATIVES AND THEIR USES FOR PREPARING ION-EXCHANGING MEMBRANES

(75) Inventors: Christophe Michot, Grenoble (FR); Michel Armand, Montreal (CA)

(73) Assignee: Hydro Quebec (CA)

( * ) Notice: Subject to any disclaimer, the term of this patent is extended or adjusted under 35 U.S.C. 154(b) by 1176 days.

(21) Appl. No.: 12/146,903

(22) Filed: Jun. 26, 2008

(65) Prior Publication Data

US 2009/0076178 A1    Mar. 19, 2009

Related U.S. Application Data

(63) Continuation of application No. 10/858,208, filed on Jun. 2, 2004, now abandoned, which is a continuation of application No. 10/200,528, filed on Jul. 23, 2002, now abandoned, which is a continuation of application No. 09/390,650, filed on Sep. 7, 1999, now abandoned, which is a continuation of application No. PCT/CA99/00083, filed on Apr. 29, 1999.

(30) Foreign Application Priority Data

Jan. 30, 1998    (CA) .................................... 2228466
Apr. 28, 1998    (CA) .................................... 2236196

(51) Int. Cl.
    *C08F 12/30*    (2006.01)
(52) U.S. Cl.
    USPC ........................... 526/243; 526/240; 526/241
(58) Field of Classification Search
    USPC ......................... 526/243, 240, 241
    See application file for complete search history.

(56) References Cited

U.S. PATENT DOCUMENTS

| | | | | | |
|---|---|---|---|---|---|
| 3,676,143 | A | * | 7/1972 | Himmelmann et al. ...... | 430/426 |
| 4,505,997 | A | * | 3/1985 | Armand et al. ............... | 429/314 |
| 5,281,680 | A | | 1/1994 | Grot | |
| 5,414,117 | A | | 5/1995 | Armand et al. | |
| 5,449,697 | A | | 9/1995 | Noaki et al. | |
| 5,463,005 | A | * | 10/1995 | Desmarteau .................. | 526/240 |
| 5,627,292 | A | * | 5/1997 | Armand et al. ............... | 549/555 |
| 5,721,328 | A | * | 2/1998 | Armand et al. ............... | 526/243 |
| 5,916,475 | A | | 6/1999 | Michot et al. | |
| 6,025,092 | A | | 2/2000 | Doyle et al. | |
| 6,288,187 | B1 | * | 9/2001 | Armand ........................ | 526/240 |

FOREIGN PATENT DOCUMENTS

| | | | |
|---|---|---|---|
| DE | 1942562 | * | 4/1971 |
| DE | 1942562 A1 | | 4/1974 |
| JP | 63 013 056 A | | 1/1988 |
| JP | 06-509811 A | | 11/1994 |
| JP | 08-143531 A | | 6/1996 |
| JP | 08-511274 A | | 11/1996 |
| JP | 2000-508008 A | | 6/2000 |
| WO | 95/26056 A1 | | 9/1995 |
| WO | 97/25369 A1 | | 7/1997 |
| WO | 97/35929 A1 | | 10/1997 |
| WO | 98/50349 A1 | | 11/1998 |
| WO | 99/05126 A1 | | 2/1999 |
| WO | 99/38842 A1 | | 8/1999 |
| WO | WO-99/38842 | * | 8/1999 |

OTHER PUBLICATIONS

Notice of Reason for Rejection for Japanese Patent Application No. 11-538750 with a mailing date of Apr. 2, 2009.
Decision of Final Rejection for Japanese Patent Application No. 11-538750 with a mailing date of Nov. 24, 2009.
"Novel perfluorinated ionemers and Ionenes", Darryl D. DesMarteau, Journal of Fluorine Chemistry (1995) p. 203-208.
"The Double Cycloaddition of Disulfene and Its Related Reactions", Joki Hirai et al., Bulletin of the Chemical Society of Japan, vol. 43, 1970, p. 488-491.
"N-substituted sulfamates", Hachiro Yamaguchi, Chemical Abstracts, Columbus, Ohio, vol. 60, No. 3 (1964).
Database Crossfire, Beistein Institut für Literatur des organischen Chemie XP002103385, 1988-1998 edition.
Database Crossfire, Beistein Institut für Literatur des organischen Chemie XP002103386, 1988-1998 edition.
Pamela L. Heinze and Donald J. Burton, "Paliadium-Catalyzed Cross-Coupling of Perfluoroalkenylzinc Regents with Aryl Iodides, A New, Simple Synthesis of . . . Stereoselective preparation of 1-Arylperfluoropropenes", J. of Organic Chemistry, 53, (1988) 2714-2720.

* cited by examiner

*Primary Examiner* — Peter D. Mulcahy
*Assistant Examiner* — Henry Hu
(74) *Attorney, Agent, or Firm* — Katten Muchin Rosenman LLP

(57) ABSTRACT

The present invention is concerned with novel ion-exchange membranes, their method of preparation and their uses. The membranes are made of a polymer obtained from a monomer or a mixture of bifunctional monomers of general formula $[\text{T-SO}_2\text{—Y—SO}_2\text{-T'}]^-\text{M}^+$. The polymers are useful in an alkali-chloride electrolysis process, as a separator in an electrochemical preparation of inorganic and organic compounds, as a separator between an aqueous and an organic phase, or as a catalyst for Diels-Alder additions, Friedel-Craft reactions, aldol condensations, cationic polymerizations, esterifications, and acetal formations.

4 Claims, No Drawings

CROSS-LINKABLE BI-SULPHONYL DERIVATIVES AND THEIR USES FOR PREPARING ION-EXCHANGING MEMBRANES

This application is a continuation of U.S. patent application Ser. No. 10/858,208 filed Jun. 2, 2004, which is a continuation of U.S. patent application Ser. No. 10/200,528 filed Jul. 23, 2002, abandoned, which is a continuation of U.S. patent application Ser. No. 09/390,650, filed on Sep. 7, 1999, which is a continuation of International Application No. PCT/CA99/00083, filed on Jan. 29, 1999. The contents of these applications are incorporated herein by reference.

FIELD OF THE INVENTION

The present invention is concerned with cationic ion-exchange resins, particularly in the form of membranes, eventually perfluorinated, useful in particular in electrochemical applications such as fuel cells, alkali-chloride processes, electrodialysis, ozone production, as well as any other application related to the dissociation of anionic centers linked to the membrane, such as heterogeneous catalysis in organic chemistry.

BACKGROUND OF THE INVENTION

Because of their chemical inertia, ion-exchange membranes partially or completely fluorinated are usually chosen for alkali-chloride processes or fuel cells consuming hydrogen or methanol. Such membranes are commercially available under trade names like Nafion™, Flemion™, Dow™. Other similar membranes are proposed by Ballard Inc. in application WO 97/25369 that describes copolymers of tetrafluoroethylene and perfluorovinylethers or trifluorovinylstyrene. The active monomers from which these copolymers are obtained bear chemical functions that are the precursors of ionic groups of the sulfonate or carboxylate type. Example of such precursors are:

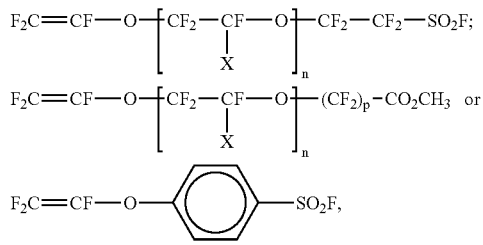

wherein

X is F, Cl or $CF_3$;

n is 0 to 10 inclusively; and p is 1 or 2.

Aromatic polymers of the polyimide or sulfonated polyether sulfone type have also been considered, for example:

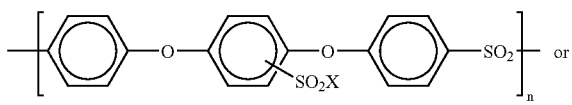

-continued

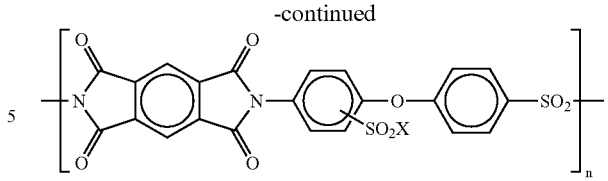

Once obtained, the copolymer containing the above precursors is molded, for example in the form of sheets, and converted into an ionic form through hydrolysis, to give species of the sulfonate or carboxylate type. The cation associated to the sulfonate and carboxylate anion include the proton, an alkali metal cation ($Li^+$, $Na^+$, $K^+$); an alkaline-earth metal cation ($Mg^{2+}$, $Ca^{2+}$, $Ba^{2+}$); a transition metal cation ($Zn^{2+}$, $Cu^{2+}$); $Al^{3+}$; $Fe^{3+}$; a rare earth cation ($Sc^{3+}$, $Y^{3+}$, $La^{3+}$); an organic cation of the "onium" type, such as oxonium, ammonium, pyridinium, guanidinium, amidinium, sulfonium, phosphonium, these organic cations being optionally substituted by one or more organic radicals; an organometallic cation such as metallocenium, arene-metallocenium, alkylsilyl, alkylgermanyl or alkyltin.

Such membranes suffer from many important disadvantages.

A) Although the copolymers forming the membrane are insoluble in their ionic form, the membrane does not have a good dimensional stability and swells significantly in water or polar solvents. These copolymers form inverted micellia only when heated at high temperatures in a specific mixture water-alcohol that, after evaporation, allows the production of a film. However, this film regenerated in the solid form does not have good mechanical properties.

B) Tetrafluoroethylene (TFE) is a hazardous product to handle, because its polymerization is performed under pressure and can cause uncontrolled reactions, particularly in the presence of oxygen. Because of the difference of boiling points between the two monomers forming the copolymer, as well as their polarity difference, it is difficult to obtain a statistical copolymer corresponding to the addition rate of each monomer.

C) The ionic groups in high concentration on the chain have a tendency to cause solubilisation of the copolymer. To prevent this phenomenon, the concentration of ionic groups is kept fairly low by adding an important molar fraction of TFE monomers and/or by increasing the secondary chains length (n>1), with the end result that the concentration of the exchangeable ion groups are less than 1 milliequivalent per gram. Consequently, the conductivity is relatively low and highly sensitive to the water content of the membrane, particularly when the latter is acidified for applications in a fuel cell.

D) The penetration of methanol and oxygen through the membrane is high, because the perfluorocarbonated portion of the polymer allows an easy diffusion of the molecular species, which will chemically react at the opposite electrode and cause a loss of faradic efficiency, mainly in methanol fuel cells.

Non-fluorinated systems like sulfonated polyimides or sulfonated polyether sulfones have the same drawbacks because one must compromise between the charged density, and thus the conductivity, and the solubility or excessive swelling.

SUMMARY OF THE INVENTION

The present invention is concerned with a bifunctional monomer of the general formula

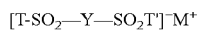

wherein

T and T' are the same or different and comprise an organic radical bearing at least one polymerization active function such as an insaturation or a cycle susceptible of opening;

$M^+$ comprises an inorganic or organic cation;

Y comprises N or CQ wherein Q comprises H, CN, F, $SO_2R^3$, $C_{1-20}$ alkyl substituted or unsubstituted; $C_{1-20}$ aryl substituted or unsubstituted; $C_{1-20}$ alkylene substituted or unsubstituted, wherein the substituent comprises one or more halogens, and wherein the chain comprises one or more substituents F, $SO_2R$, aza, oxa, thia or dioxathia; and $R^3$ comprises F, $C_{1-20}$ alkyl substituted or unsubstituted; $C_{1-20}$ aryl substituted or unsubstituted; $C_{1-20}$ alkylene substituted or unsubstituted, wherein the substituent comprises one or more halogens.

In a preferred embodiment, $M^+$ comprises the proton, a metal cation such as an alkaline metal, an alkaline-earth metal, a rare earth or a transition metal; an organometallic cation such as a metallocenium, an arene-metallocenium, an alkylsilyl, an alkylgermanyl or an alkyltin; or an organic cation optionally substituted with one or more organic radicals. Examples of preferred organic cations include $R''O^+$ (onium), $NR''^+$ (ammonium), $R''C(NHR'')_2^+$ (amidiniun), $C(NHR'')_3^+$ (guanidinium), $C_5R''N^+$(pyridinium), $C_3R''N_2^+$ (imidazolium), $C_2R''N_3^+$ (triazolium), $C_3R''N_2^+$ (imidazolinium), $SR''^+$ (sulfonium), $PR''^+$ (phosphonium), $IR''^+$ (iodonium), $C_6R''{}_3C^+$ (carbonium), wherein $R''$ comprises:

a proton, an alkyl, an alkenyl, an oxaalkyl, an oxaalkenyl, an azaalkyl, an azaalkenyl, a thiaalkyl, a thiaalkenyl, a dialkylazo, a silaalkyl, optionally hydrolysable, a silaalkenyl optionally hydrolysable, each of these being straight, branched or cyclic and comprising from 1 to 18 carbon atoms;

aliphatic heterocyclic or cyclic radicals comprising from 4 to 26 carbon atoms comprising optionally at least one lateral chain comprising one or more heteroatoms such as nitrogen, oxygen or sulfur;

an aryl, an arylalkyl, an alkylaryl or an alkenylaryl of from 5 to 26 carbon atoms optionally comprising one or more heteroatoms in the aromatic nucleus or in a substituent;

groups comprising several heterocyclic or aromatic nuclei, condensed or not, optionally containing one or more nitrogen, oxygen, sulfur or phosphorus; and when an organic cation comprises at least two radicals $R''$ different from H, these radicals can form together a cycle aromatic or not, optionally containing the centre bearing the cationic charge.

The invention further comprises an ion exchange polymer that is a solid ion conductor obtained from a monomer or a mixture of monomers bifunctional as defined above. The monomer or the mixture of monomers can be copolymerized with at least one monofunctional monomer, preferably of formula $[T-SO_3]^-M^+$ or $[T-SO_2-Y-SO_2-W]^-M^+$ wherein T, Y and $M^+$ are as defined above, and W is a monovalent alkyl, alkenyl, aryl, arylalkyl, alkylaryl of from 1 to 12 carbon atoms optionally comprising one or more substituents oxa, aza or thia.

The invention further relates to a process for the preparation of a polymer from monomers or a mixture of the monomers mentioned above, wherein the monomers or mixtures of monomers are polymerized in solution in a solvent, the polymer formed remaining plasticized homogeneously by the solvent. The monomer or mixture of monomers are preferably polymerized in the form of an emulsion in non-miscible solvents.

The process of the present invention is particularly advantageous over the prior art processes, because it provides for a polymer that remains plasticized homogeneously in the solvent. This is a rare phenomenon and completely unexpected, which can be explained by the strong interactions between the charges and the solvent.

DETAILED DESCRIPTION OF THE INVENTION

The present invention relates to the use of perfluoro-di (vinylethers) bearing imide or sulfone functions highly dissociated, such as di(sulfonylmethane) or tri(sulfonylmethane), as a base for preparing cross-linked ion exchange resins obtained directly in a final form, for example a film or a hollow fiber (hereunder referred to as "membrane"), and having a high ionic functions density, resulting in an increased conductivity. The polymerization can be performed in a concentrated solution of the monomer in the form of a salt. The polymers obtained do not have the disadvantages of the perfluorinated ionomers of the prior art, because they have a good dimensional stability in the presence of solvents, including water and polar solvents, while maintaining an excellent conductivity because of the high concentration of ionic groups. In addition, the cross-linking creates an excellent barrier with respect to the diffusion of molecular species, particularly oxygen or methanol, as well as other organic combustibles. The presence of TFE is not necessary or can be minimized, thus reducing the risks during the manufacture process. The polymers can be converted into extremely thin membranes, i.e., with a thickness on the order of 50 µm or less, while maintaining a good mechanical behaviour while conventional membranes of the same thickness have no mechanical behaviour at all. The process of the present invention therefore represents an efficient use of the monomers costwise.

The electrochemical applications of the membranes obtained from the cross-linked polymers of the present invention require electrode materials and/or catalysts in intimate contact with the membrane used as the electrolyte. Upon use of these membranes, the electrode materials can be easily deposited on either one or both sides of the membrane during the fabrication, eventually during the polymerization step. The electrode materials can also be applied on a membrane already formed. This coating can be performed by applying a solution of at least one monomer of the present invention in an appropriate solvent, followed by polymerization, or the application of a solution or a suspension of a polymer bearing eventually ionic functions. In all these cases, the polymers present on the electrodes advantageously act as a binder for the active materials, conductors or catalysts.

In a preferred embodiment, the imide function, i.e., when Y=N, as well as polysulfonyl carbanions, and to a lesser degree perfluorosulfonate anions having a strong electronic affinity and highly dissociated, allow an increase in the catalytic activity of the cations, specific to several reactions. The polymers of the invention are therefore useful as catalyst support. In the form of a cross-linked material, the membrane or the material of the membrane, for example in the form of a powder or granules, and containing active cations in catalysis, are easily separated mechanically from the reaction medium after completion of the reaction. Examples of reactions that can be catalyzed include Diels-Alder additions, Friedel-Craft reactions, aldol condensation, cationic polymerizations, esterifications, acetal formations, etc.

Examples of preferred monomers include:

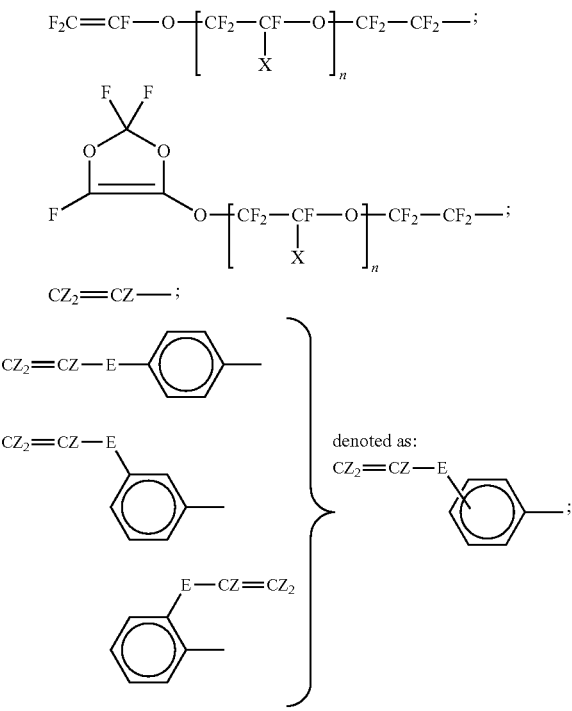

wherein
X represents F, Cl, or $CF_3$;
n varies between 0 and 10 inclusively;
E is absent, O, S, $SO_2$; and
Z is F or H.

The monomers of the invention can be obtained from different processes. For example, the monomers of the imide type can be obtained in the following manner:

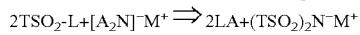

or

wherein L is a leaving group, for example a halogen, a thiocyanate, or an electrophilic group containing at least one heteroatom, such as N-imidazolyle, N-triazolyl, or R—$SO_2O$— wherein R is $C_{1-20}$ alkyl or $C_{1-20}$ alkylene substituted or unsubstituted, wherein the substituent is one or more halogens; and wherein the chain comprises one or more substituents selected from aza, oxa, thia, or dioxathia; and A is an element or a fraction of an element corresponding to the cation $M^+$, and comprises hydrogen, a trialkylsilyl group, a trialkyltin or tertioalkyl group, and wherein the alkyl group comprises from 1 à 6 carbon atoms.

In the same manner, the monomers comprising carbon atoms, i.e., when Y=CQ, are obtained from similar reactions:

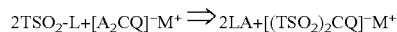

wherein L, T, Q, A and M are as defined above.

The tertioalkyl radical in the definition of A above is advantageous because it is the precursor of an alkene eliminating itself from the reaction medium and a proton. For example, if it is a tertiobutyl, the following reaction is observed:

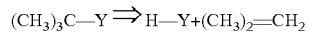

The trialkylsilyl group is advantageous when the leaving group L is fluorine, because of the high formation enthalpy of the Si—F bond.

When A is a proton or a proton precursor, such as a tertioalkyl radical, it is advantageous to perform the reaction in the presence of a hindered base, such as a tertiary base. Examples of such bases are 1a triethylamine, di-isopropylamine, quinuclidine, 1,4-diazobicyclo[2,2,2]octane (DABCO), pyridine, alkylpyridines, dialkylaminopyridines, N-alkylimidazoles, imidazo[1,1-a]pyridine, amidines such as 1,5-diazabicyclo[4,3,0]non-5-ene (DBN) or 1,8-diazabicyclo[5,4,0]undec-7-ene (DBU), guanidines such as tetramethylguanidine, 1,3,4,7,8-hexahydro-1-methyl-2H-pyrimido-[1,2-a]pyrimidine (HPP).

In several instances, the potassium salts of the monomer of the invention are insoluble or slightly soluble in water, and can be precipitated therein from more soluble salts, i.e., salts $H^+$, $Li^+$ or $Na^+$, and subsequently purified by recrystallization. The recrystallization can be performed in water, alone or in admixture with a miscible solvent such as acetonitrile, dioxanne, acetone or THF.

The alkylammonium salts, particularly the tetraalkylammonium or imidazolium salts, are usually insoluble in water and can therefore be extracted with various solvents, preferably halogenated, such as dichloromethane, dichloroethane, trichloroethane, 1,1,1,2-tetrafluoroethane, etc.

It is understood that any function of the monomer that can interfere with the reaction leading to the formation of a bond $SO_2$—Y—$SO_2$ is protected beforehand according to protecting techniques well known to those skilled in the art. For example, the perfluorovinylether groups can be halogenated, particularly chlorinated or bromated, to lead to a non-reactive perhaloether. The perfluorovinylether is eventually regenerated according to various processes well known to those skilled in the art, for instance through an electrochemical reaction, with a reducing agent such as zinc powder, an alloy of bronze zinc-copper, or the tetrakis(dimethylamino)ethylene.

The following bifunctional monomers illustrate preferred monomers of the invention.

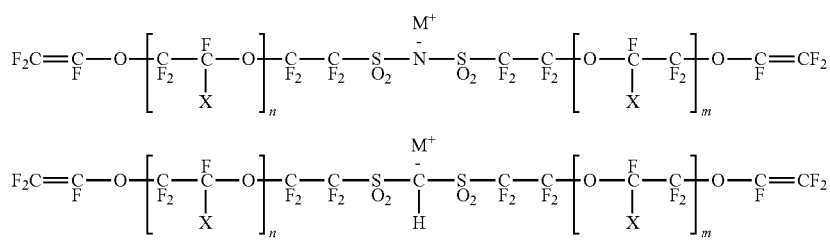

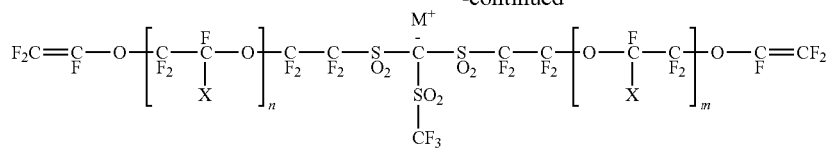

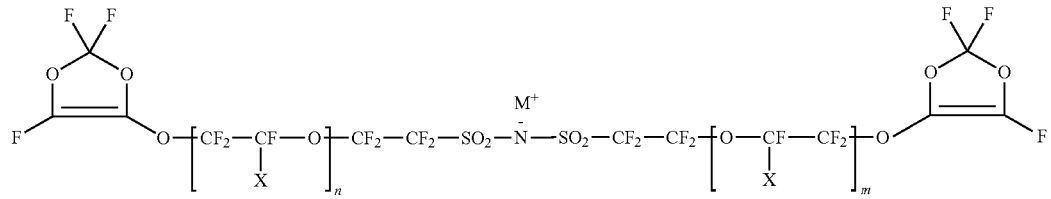

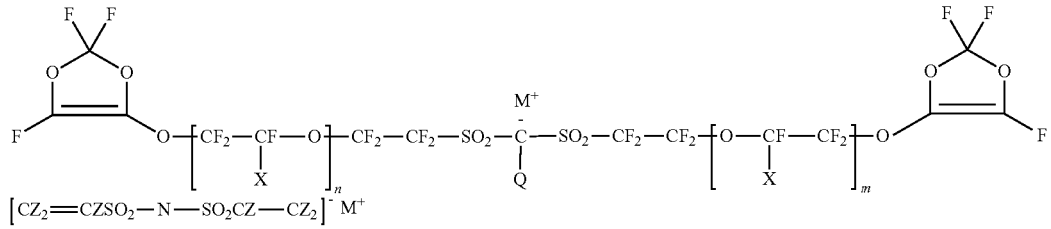

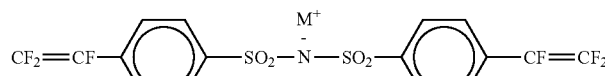

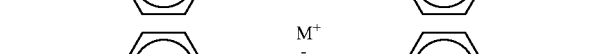

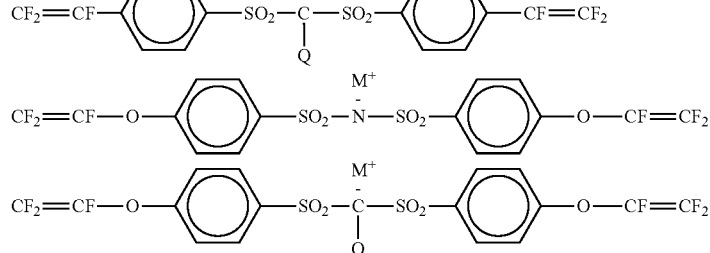

wherein $M^+$, Z, Q, X, and Y are as defined above, and n and m are identical or the same or different and vary between 0 and 10 inclusively.

Practically, the ion exchange membranes are obtained through homo- or copolymerization of the bifunctional monomers of the present invention. For the copolymers, the comonomers are advantageously selected from the salts of the functional monomers of the following general formula:

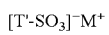

or

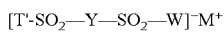

wherein T', Y, $M^+$ are as defined above and W has the same definition as Q.

Examples of preferred monofunctional monomers of the present invention for a copolymerization include:

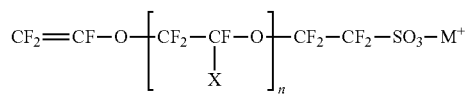

-continued

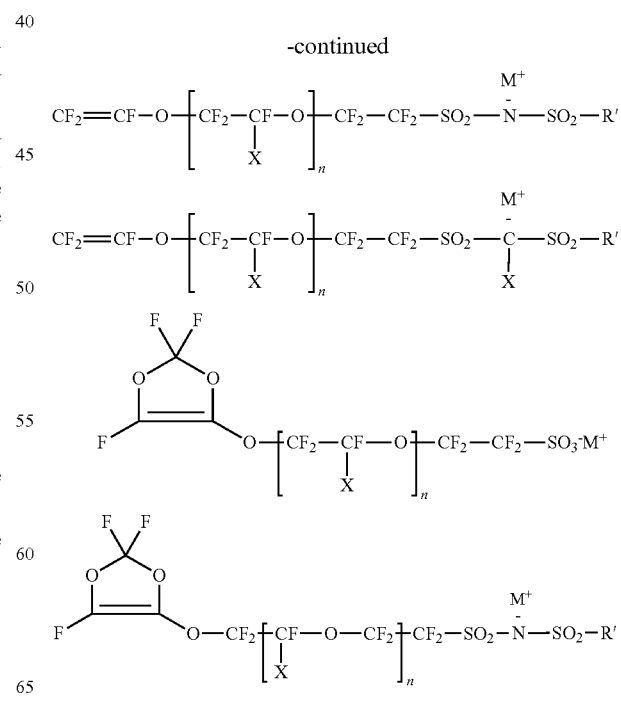

-continued

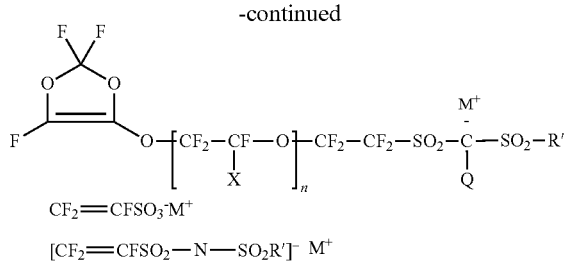

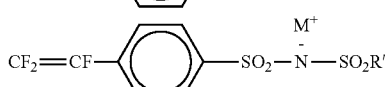

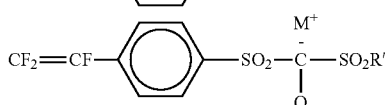

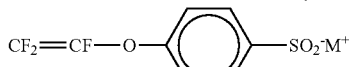

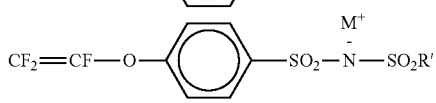

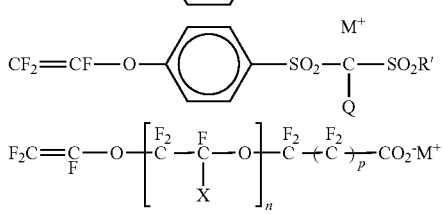

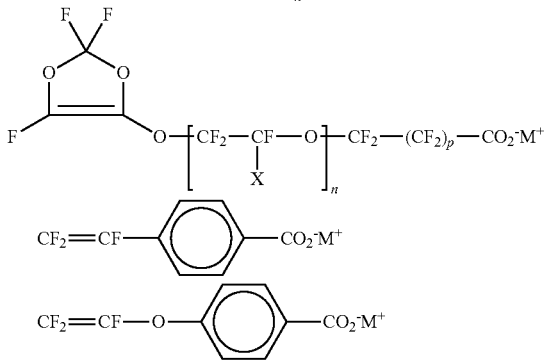

wherein M, O, X, and n are as defined above, R' is a monovalent organic radical comprising from 1 to 12 carbon atoms, preferably perfluorinated, eventually possessing one or more substituents oxa, aza, thia, or dioxathia; and p is 1 or 2.

Advantageously, the polymerization and copolymerization reactions are performed in a solvent of the monomers. The monomers are generally soluble in most usual polar solvents, i.e., water, lower aliphatic alcohols, acetone, methyl ethyl ketone, cyclic ketones, propyl and ethyl carbonate, γ-butyrolactone, N-alkylimidazole, fluoroalkane, and mixtures thereof. Further, the selection of M allows the optimization of the solubility of the monomers because of the cation-solvent interaction. It is understood that after completion of the polymerization, the exchanges of M are carried out according to conventional techniques used in the field of ion exchange resins. Inorganic or organic solid additives in the form of powder or fibers can be added during manufacturing to improve the mechanical properties of the polymers, to act as a pore formation agent, or as a catalyst support (e.g., platinum deposited on carbon particles).

The following examples are provided to illustrate preferred embodiments of the invention, and should not be construed as limiting its scope.

EXAMPLES

Example 1

Under nitrogen atmosphere, 25 g of p-iodobenzene sulfonyl chloride are treated with 1.44 g of lithium nitride in 125 ml or anhydrous DMF. After 24 hours under constant mechanical agitation, the reaction mixture is filtered and the solvent is evaporated under reduced pressure at 80° C. The solid residue containing the 4-iodophenylsulfonimide lithium salt is dissolved in 100 ml of water, filtered and acidified with sulfuric acid to reach a pH of 1. The 4-iodophenylsulfonimide is extracted with four aliquots of 100 ml of ether, the organic phase is subsequently combined and the ether is evaporated. 4-iodophenylsulfonimide is purified by crystallization in water and the zinc salt is prepared by adding zinc carbonate in a stoichiometric amount. The salt is dried under vacuum at 80° C.

The organozincic $CF_2$=CFZnBr is synthesized under argon in DMF according to the procedure published in J. of Organic Chemistry, 53, 2714, (1988) starting from $CF_2$=CFBr (10 g) in a thermostated reactor. 18 g of the zinc salt as prepared previously in DMF are added to the solution of the organometallic mixed with 160 mg of benzylideneacetone palladium (0) and 190 mg of triphenylphosphine acting as a co-catalyst, while maintaining the temperature below 65° C. The reaction is carried out for 4 hours at this temperature and the solvent is evaporated under reduced pressure at 80° C. The solid residue is washed with water, filtered and treated with 10 g of potassium carbonate in 100 ml of water. The white suspension containing the zinc carbonate is evaporated under reduced pressure at 60° C. The potassium salt is extracted with a mixture acetonitrile-dimethoxyethane (50:50 v/v), and the solvent is evaporated. The potassium salt

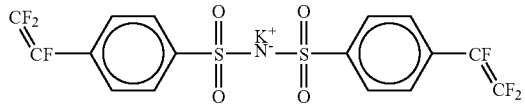

is purified by recrystallization in water and transformed into the lithium salt by double exchange with the lithium tetrafluoroborate in acetonitrile wherein $KBR_4$ is insoluble.

Example 2

A solution of 1 g of the lithium salt of example 1, 10 g of lithium 4-trifluorovinylbenzene sulfonate, 250 mg of Irgacure 651® in 35 ml of a mixture of propylene carbonate and diglyme (bis[methoxyethylether]) (50:50 v/v) are spread in the form of a film of the thickness of 180 microns on a polypropylene support. Under argon sweeping, the solution is submitted to UV rays produced by a Hanovia® type lamp having its maximum emission at 254 nm so that the illumination corresponds to 80 mWcm$^{-2}$. The solution polymerizes in the form of an elastic gel. Polymerization is carried out for 5 minutes and the film is removed from its support and washed with water and nitric acid 2M at 60° C. to eliminate the organic solvents and the polymerization residues. The conductivity of the membrane measured between 60 and 100% humidity is higher than $10^{-2}$ Scm$^{-1}$. The membrane dimensions are stable in a wide domain of humidity content as a result of the high concentration of cross-linking knots.

Example 3

30 g of 4-iodobenzenesulfonyl chloride, 15 g of trifluoromethane-sulfonamide and 23 g of 1,4-diazabicyclo[2,2,2]octane are dissolved in 200 ml of anhydrous acetonitrile and maintained under magnetic agitation for 48 hours at 25° C. The suspension is filtered and the acetonitrile is evaporated. The solid residue is washed with a minimum quantity of water to which is added 100 ml of a saturated solution of KC1. The potassium salt precipitate is separated by filtration and purified by recrystallization in boiling water. In a similar manner to that of Example 2, the iodine in para position is replaced with a group $CF_2$=CF by coupling the organozincic $CF_2$=CFZnBr in the presence of a palladium-based catalyst. The potassium salt

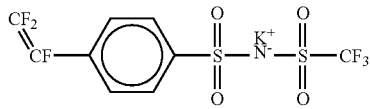

is purified by recrystallization in water and transformed into the lithium salt. A solution of 8.8 g of this salt and 1 g of the monomer of Example 1 in the form of the lithium salt are dissolved in 40 ml of γ-butyrolactone, spread in the form of a film of 150 microns thick on a polypropylene support and polymerized in the conditions of Example 2. The film is removed from its support and washed with water and nitric acid 2 M at 60° C. to eliminate the γ-butyrolactone and perform the exchange $Li^+ \Rightarrow H^+$. In a similar manner, the mixture of salts in identical proportions in γ-butyrolactone in suspension in decane are polymerized with tridecylmethyl ammonium persulfate acting as a tensioactive and free radical generator at 60° C. A latex of particles of dimension close to 20 μm is thus obtained, separated by filtration and treated as above to perform the exchange $Li^+ \Rightarrow H^+$.

Example 4

50 g of perfluorovinyloxy-ethanesulfonyl fluoride $CF_2$=CFOCF$_2$CF$_2$SO$_2$F in 300 ml of carbon tetrachloride are treated with an excess of chlorine in a quartz recipient under UV illumination. The addition product on the double bond $CF_2(Cl)CF(Cl)OCF_2CF_2SO_2F$ is purified by distillation. In a high density polyethylene recipient with thick side walls (Nalgene®) are added 35 g of $CF_2(Cl)CF(Cl)OCF_2CF_2SO_2F$ as prepared above, 125 ml of anhydrous THF and 1.74 g of lithium nitride and 36 zircon grinding cylinders (@ 1 cm$^3$). After 24 hours of agitation in a roll grinder, 10 g of the powder of an alloy zinc-copper (10% Cu) are added and agitated and the agitation is carried out for a further 24 hours. The final product is filtered and the solvent is evaporated under reduced pressure at 40° C. The residue is mixed with a solution of 10% of potassium chloride in water. The precipitate is washed, filtered and recrystallized in a mixture water-ethanol (50:50 v/v). The lithium salt Li[(CF2=CFOCF$_2$CF$_2$SO$_2$)$_2$N] is obtained by exchange with LiBF$_4$ in triglyme.

The lithium perfluorovinyloxy-ethylsulfonate $CF_2$=CFOCF$_2$CF$_2$SO$_3$Li is prepared in a similar manner from the perfluorovinyloxy-ethanesulfonyl fluoride by treatment with lithium trimethylsilanoate in triglyme and filtered.

Example 5

A cross-linked perfluorinated membrane is prepared in a homogeneous phase by copolymerization of 4 g of the lithium salt Li[(CF$_2$=CFOCF$_2$CF$_2$SO$_2$)$_2$N] of Example 4, with 24 g of lithium perfluorovinyloxy-ethanesulfonate in 60 ml of triglyme. 1.5 g of nanoparticles of fumed silica (average size 70 Å) are added and dispersed under mechanical agitation in a ball mill. The radical initiator is trichloroacetyl peroxide in proportion of 1% molar with respect to the monomers. The solution is spread on a polypropylene support in order to form a film of a thickness of 100 microns. The polymerization/cross-linking step is performed by heating at 80° C. under deoxygenated nitrogen atmosphere. The film obtained is removed from its support and washed with water and nitric acid 2M at 60° C. to eliminate the organic solvents and the polymerization residues, as well as for replacing the Li$^+$ cations with H$^+$. The conductivity of the membrane at 95% humidity is about $10^{-2}$ Scm$^{-1}$. The methanol permeation is lower in line-up in order of size by 1 with respect to a Nation 117® membrane of a similar thickness.

Example 6

17.5 g of perfluorovinyloxyethanesulfonyl fluoride $CF_2(Cl)CF(Cl)OCF_2CF_2SO_2F$ treated with chlorine under UV rays are poured in a Nalgene® recipient in 100 ml of anhydrous THF are added with 1.2 g of aluminum carbide (C$_3$Al$_4$) along with 36 zircon grinding cylinders (about 1 cm$^3$). After 48 hours of agitation in a roll grinder, 10 g of zinc powder are added and the agitation is carried out for further 48 hours. The final product is filtered and the solvent is evaporated under reduced pressure at 40° C. The residue is mixed with a solution of 10% of potassium chloride in water. The precipitate is washed, filtered and recrystallized in a water-ethanol mixture (50:50 v/v). By exchange with LiBF$_4$ the lithium salt Li[(CF$_2$=CFOCF$_2$CF$_2$SO$_2$)$_2$CH] is obtained. This difunctional monomer can polymerize in a manner similar to that of Example 4, and is advantageously used when highly acidic functions with low hygroscopy are preferred.

Example 7

Perfluoro(4-methyl-3,6-dioxaoct-7-ene)sulfonyl fluoride (Synquest Research Chemicals) is treated with lithium nitride in the conditions of Example 4 after protecting the double bond with bromine. The lithium salt Li[(CF$_2$=CFOCF$_2$CF(CF$_3$)OCF$_2$CF$_2$SO$_2$)$_2$N] is obtained after reduction with zinc and purification to the potassium salt step obtained as an intermediate. The lithium perfluoro(4-methyl-3,6-dioxaoct-7-ene)sulfonate is obtained in a similar manner by reaction of lithium silanoate on the sulfonyl fluoride in dibutyldiglyme ([C$_4$H$_9$OC$_2$H$_4$]$_2$O). A cross-linked membrane is obtained by polymerization of a mixture of 3 g of the divinylic monomer and 18 g of the monovinylic perfluorosulfonate, 800 mg of fumed silica (7 nm) in 50 ml of dibutyldiglyme. The solution is spread in the form of a film and the polymerization is carried out with the photoinitiator Irgacure 651®. Under argon sweeping, the solution is submitted to UV rays in the conditions of Example 2. The membrane is washed with ethanol and water and the lithium ions are exchanged by HCl 5M in water.

Example 8

The perfluoro(4-methyl-3,6-dioxaoct-7-ene)sulfonyl perfluoride of Example 7 is treated with aluminum carbide in the conditions of Example 6. After treatment with potassium carbonate and elimination of the aluminum hydroxide formed, the lithium salt $Li[(CF_2=CFOCF_2CF(CF_3)OCF_2CF_2SO_2)_2CH]$ is obtained after purification of the potassium salt and exchange in the presence of $LiBF_4$ in THF. Similar results are obtained by using, instead of aluminum carbide, the Nysted reagent $(Zn_3Br_2(CH_2)_2, THF)$. As for its nitrogenated analogue, this monomer is susceptible of homopolymerizing or copolymerizing with tetrafluoroethylene or monofunctional ionic monomers. A cross-linked copolymer with the lithium perfluoro(4-methyl-3,6-dioxaoct-7-ene) sulfonate (10:90 molar) is obtained in a similar manner to that of Example 7.

Example 9

To 3.73 g of trifluoromethylmethylsulfone $CF_3SO_2CH_3$ in 50 ml of THF are added at 0° C. 600 mg of sodium hydride and 3.15 ml of chlorotrimethylsilane. After precipitation of the sodium chloride formed, the supernatant liquid is filtered and 20 ml of a solution of 2.5 M of butyllithium in hexane are added. The addition product of chlorine on the vinylic double bond $CF_2(Cl)CF(Cl)OCF_2CF_2SO_2F$ is prepared in the same manner as in Example 4. In a high density polyethylene recipient with thick side walls (Nalgene®) are added to the dilithiated derivative of the sulfone in THF as prepared, 6.7 ml of tetramethylethylene diamine (TMDA) and 17.5 g of $CF_2(Cl)CF(Cl)OCF_2CF_2SO_2F$ obtained by adding chlorine on the double bond of the perfluorovinyloxyethanesulfonyl in a manner similar to that of Example 4. 36 zircon grinding cylinders (about 1 cm³) are added to favour the heterogeneous solid-liquid reaction. After 24 hours of agitation in a roll grinder, 5 g of a zinc-copper alloy powder (10% Cu) are added and the agitation is continued for a further 24 hours. The final product is filtered and the solvent is evaporated under reduced pressure at 40° C. The residue is mixed with a solution of potassium chloride 10% in water. The precipitate is washed, filtered and recrystallized in a mixture water-ethanol (50:50 v/v). The lithium salt $Li[(CF_2CFOCF_2CF_2SO_2)_2CSO_2CF_3]$ is obtained by exchange with $LiBF_4$ in triglyme. The monofunctional monomers of lithium bis(trifluomethanesulfonyl-(trifluoperfluorovinyloxy-ethylsulfonyl)methylide $Li[CF_2=CFOCF_2CF_2SO_2C(SO_2CF_3)_2]$ and lithium trifluoromethanesulfonyl-(trifluoroperfluorovinyloxy-ethylsulfonylimidide $Li[CF_2=CFOCF_2CF_2SO_2N(SO_2CF_3)]$ can be obtained in a similar manner by reacting $CF_2(Cl)CF(Cl)OCF_2CF_2SO_2F$ prepared in Example 4 on dilithiated derivatives of the disulfone $Li_2C(SO_2CF_3)_2$ and of the sulfonamide $Li_2NSO_2CF_3$ respectively.

Example 10

Starting with the perfluoro(4-methyl-3,6-dioxaoct-7-ene) sulfonyl fluoride of Example 8, are obtained by action of the reagent of Example 9
$Li[(CF_2=CFOCF_2CF(CF_3)OCF_2CF_2SO_2)_2CSO_2CF_3)]$bifunctional;
$Li[CF_2=CFOCF_2CF(CF_3)OCF_2CF_2SO_2C(SO_2CF_3)_2]$ monofunctional;
$Li[CF_2=CFOCF_2CF(CF_3)OCF_2CF_2SO_2N(CSO_2CF_3)]$ monofunctional.

These monomers allow for the preparation of cross-linked copolymers incorporating at least the bifunctional monomer and one of the monofunctional monomers selected from those of Examples 7, 9 or 10 that commonly have perfluorovinylether functions of identical reactivity.

Example 11

The salt of Example 7 $Li[(CF_2=CFOCF_2CF(CF_3)OCF_2CF_2SO_2)_2N]$ is treated with 1-methyl-3-ethyl-imidazolium chloride in solution in water. A viscous liquid is decanted and extracted with dichloromethane to give

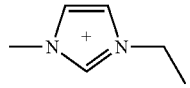

In the same manner, the monofunctional sulfonate:

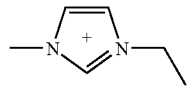

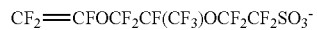

is prepared by exchange in water, as well as the salt of the radical initiator azobis(2-imidazolidium-2-methyl-propane):

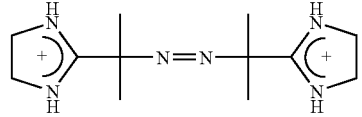

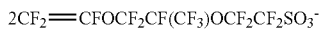

The salts are mixed in molar ratios 8:91:1 bifunctional monomer: monofunctional monomer: radical initiator. The viscous mixture is spread on a polypropylene sheet maintained at 40° C. to form a layer of 35 μm of thickness and the temperature is raised at 80° C. for 2 hours under nitrogen sweeping. The membrane thus obtained is removed from its support and the polymerization is completed by heating at 100° C. for two hours. The imidazolium ions are exchanged with the sodium ions by treatment with a solution of caustic soda 1 M and ethanol under reflux for 4 hours, leading to the degradation of the organic cation. The sodium ions are then exchanged themselves with protons by immersion in a Soxhlet type extractor containing an aqueous solution of hydrochloric acid at the azeotropic composition (20.3% by weight). The same bifunctional monomer is copolymerized with the monofunctional monomer of Example 10, $Li[CF_2=CFOCF_2CF(CF_3)OCF_2CF_2SO_2N(CSO_2CF_3)]$ and the radical initiator used above. The copolymerization is performed by inverted emulsion in decaline under strong mechanical agitation, the ratios of the active components being now 25:74:1. The system is purged with argon and after two hours at 90° C., the polymer particles are separated by filtration, washed and exchanged as above.

Example 12

17.5 g of commercial 4-hydroxybenzene sulfonic acid are treated with 4 ml of caustic soda 4M in water. The salt is dried on a rotary evaporator through azeotropic dehydration. 19.5 g of the salt obtained Na$_2$(OΦSO$_3$) (Φ=para —C$_6$H$_4$—) are suspended in 100 ml of DMF with 10.75 ml of 1,2-dibromo tetrafluoroethane and the mixture is heated to 80° C. in a Parry reactor, purged beforehand with nitrogen, under argon, and the reaction is carried out for 4 hours. The salt Na(BrCF$_2$CF$_2$OΦSO$_3$) is separated by filtration and the sulfonyl chloride is prepared by adding thionyl chloride in acetonitrile catalyzed with DMF. The imidide Na(BrCF$_2$CF$_2$OΦSO$_2$)N is prepared at 0° C. by adding caustic soda to a suspension of the acid chloride in a aqueous solution of ammonium chloride according to the equation:

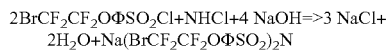
2H$_2$O+Na(BrCF$_2$CF$_2$OΦSO$_2$)$_2$N

In a high density polyethylene recipient with thick side walls (Nalgene®) are added 14 g of the imidide Na(BrCF$_2$CF$_2$OΦSO$_2$)$_2$N prepared above, 100 ml of anhydrous DMF and 4 g of a zinc alloy powder and 25 zircon grinding cylinders (about 1 cm$^3$). After 24 hours of agitation in a roll grinder, the solvent is evaporated under reduce pressure at 80° C. The residue is mixed with a saturated solution of potassium chloride in water and the precipitate of K(CF$_2$CF$_2$OΦSO$_2$)$_2$N is purified by crystallization in water. This salt can be polymerized by radicalar or thermal initiation or be included in a copolymer with the monomer Na(CF$_2$CF$_2$OΦSO$_3$) obtained by reduction with zinc of Na(BrCF$_2$CF$_2$OΦSO$_3$).

Example 13

An experimental fuel cell is fabricated from a membrane as prepared in Example 3. A nanometric dispersion of platinum on a carbon support (Degussa) is applied on both sides of the membrane by a serigraphy technique from a dispersion of the platinated carbon in a colloidal solution (5% w/w) of Nafion 117® in a mixture of light alcohols (Aldrich). The system is treated at 130° C. by applying a pressure of 20 Kgcm$^{-2}$ to ensure cohesion of the Nafion® particles. A carbon paper collector (non-woven carbon fibers) is inserted between the electrodes and the grooved stainless steel current collectors to ensure distribution of the gases. The experimental cell is tested with feeding of hydrogen saturated with water vapor at 80° C. and in oxygen, both gases being at an ordinary pressure. The tension in an open circuit is 1.2 V and the current tension curve measured on this assembly indicates 1 Acm$^{-2}$ are obtained at a tension of 0.65 V.

Example 14

An experimental fuel cell is fabricated from a membrane prepared in Example 5. The platinated carbon electrode is applied on both sides of the membrane by serigraphy of a suspension (30% by weight) of this material in a solution in diglyme comprising A) 15% by weight of the monomer of Example 4 Li[(CF$_2$=CFOCF$_2$CF$_2$SO$_2$)$_2$N]; B) 15% of the monofunctional monomer of Example 10 Li[CF$_2$=CFOCF$_2$CF(CF$_3$)OCF$_2$CF$_2$SO$_2$N(CSO$_2$CF$_3$)]; and C) 1% by weight of the initiator of Example 11.

The polymerization of the monomer of the electrodes is obtained by heating under nitrogen atmosphere at 90° C. for two hours. The assembly electrode/membrane is rinsed abundantly in an aqueous solution of hydrochloric acid 2M to eliminate the organic solvents, the unreacted monomer and the oligomers, as well as to ensure the exchange of the Li$^+$ ions of the polymer of the electrode with protons. The experimental fuel cell using such an assembly has a tension in open circuit of 1.2 V and the current tension curve measured on the assembly indicates 1 Acm$^{-2}$ are obtained at a tension of 0.72 V. Replacing the platinum of the negative electrode with a platinum-ruthenium alloy 50:50 allows the use of methanol as a combustible with a current density of 150 mAcm$^{-2}$ at a tension of 0.6 V at 100° C. The permeation of methanol in these conditions is lower than 5 μmoles·cm$^{-2}$s$^{-1}$.

Example 15

The assembly electrodes/electrolyte of an experimental fuel cell is realized in a single step by co-extrusion of the three corresponding layers in the form of monomers undergoing a co-polymerization/cross-linking. The central part is a dispersion of nanoparticles of silicon (1.5 g) in a solution of Li[(CF$_2$=CFOCF$_2$CF$_2$SO$_2$)$_2$N] (4 g), of Li[(CF$_2$=CFOCF$_2$CF$_2$SO$_3$] (24 g) in 40 ml of triglyme and 1 g of the radical initiator of Example 11. The electrodes are made of a dispersion of platinated carbon (10 g), granulated micrometric calcium carbonate (10 g), Li[(CF$_2$=CFOCF$_2$CF$_2$SO$_2$)$_2$N], (2 g), Li[(CF$_2$=CFOCF$_2$CF$_2$SO$_3$] (12 g) in 40 ml of triglyme and 0.8 g of the radical initiator of Example 11. The extrusion thicknesses are adjusted to 60 μm for the electrolyte and 30 μm for each of the electrodes. The polymerization is immediately carried out after extrusion by heating at 80° C. for 4 hours under nitrogen. The assembly is treated in a Soxhlet type apparatus with hydrochloric acid at the azeotropic composition to exchange the metallic ions. The dissolution of the calcium carbonate creates a favorable porosity for gaseous exchanges of the electrodes. The co-extruded assembly thus obtained can be cut to the desired dimensions to obtain the elements of a modular combustible cell by adding current collectors and gas injectors.

Example 16

Electrolysis of sodium chloride is performed in a cell having two compartments separated by a membrane as prepared in Example 7, the anode being of the type DSA (Dimensionally Stable Electrode) and comprising titanium coated with a layer of ruthenium oxide RuO$_2$ in contact with the membrane, the cathode being made of nickel. The ohmic drop for 2 Acm$^{-2}$ is 0.4 V and the permeation of OH— ions through the membrane is lower than 9 μmoles·cm$^{-2}$s$^{-1}$.

Example 17

The membrane of Example 4 is used for the preparation of ozone by water electrolysis on an anode of lead dioxide, the cathode is a grid of platinum, both electrodes are plated on the membrane that has the cathodic side immersed in water. The ozone faradic yield is 24% under 5 V.

Example 18

Porous ion exchange resins prepared in Examples 3 and 11 are used as chemical reaction catalysts. In the active protonic form after vacuum dehydration, the resin catalyses Friedels-Craft reactions, esterifications, acetalisations, etc. To an equimolecular mixture of anisole and acetic anhydride are added 3% by weight of the resin of Example 3 in the acidic form. The formation reaction of the 4-methoxyacetophenone is complete in 45 minutes at room temperature.

The exchange of protons for the ions of transition and rare earth metals, in particular La$^{+3}$ and Y$^{+3}$ provides a catalyst for Friedel-Craft reactions and cross-aldolisation. To an equimolecular mixture of cyclopentadiene and vinyl-methyl ketone, (10 mmoles in 30 cc of dichloromethane) are added 5% by weight of the resin of Example 11 in the form $Y^{3+}$ and dried under vacuum at 60° C. The formation reaction of the Diels-Alder condensation compound is completed at 25° C. in 30 minutes, the ratio endo/exo being near 90:10.

In both cases, the catalyst is eliminated by simple filtration, and is reusable.

While the invention has been described in connection with specific embodiments thereof, it will be understood that it is capable of further modifications, and this application is intended to cover any variations, uses or adaptations of the invention following, in general, the principles of the invention, and including such departures from the present description as come within known or customary practice within the art to which the invention pertains, and as may be applied to the essential features hereinbefore set forth, and as follows in the scope of the appended claims.

What is claimed is:

1. An ion exchange and solid ion conductor polymer obtained from a monomer having the formula:

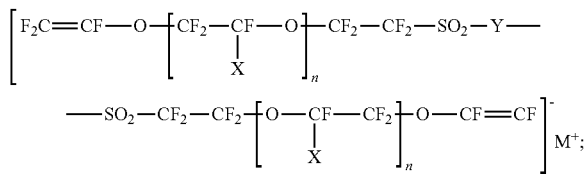

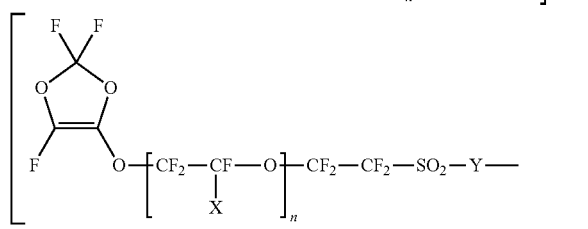

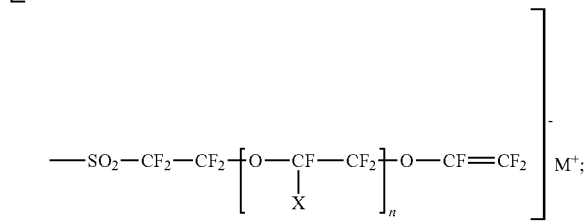

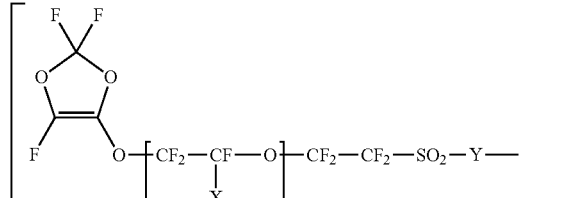

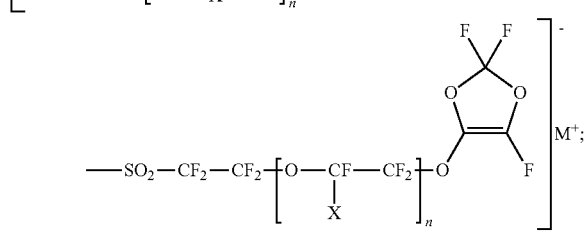

or a mixture thereof,
wherein:
$M^+$ comprises an inorganic or organic cation;
Y comprises N or CQ wherein Q comprises H, CN, F, $SO_2R^3$, $C_{1-20}$ alkyl substituted or unsubstituted; $C_{1-20}$ aryl substituted or unsubstituted; $C_{1-20}$ alkylene substituted or unsubstituted, wherein the substituent comprises one or more halogens, and wherein the chain comprises one or more substituents F, $SO_2R$, aza, oxa, thia or dioxathia; and $R^3$ comprises F, $C_{1-20}$ alkyl substituted or unsubstituted; $C_{1-20}$ aryl substituted or unsubstituted; $C_{1-20}$ alkylene substituted or unsubstituted, wherein the substituent comprises one or more halogens;

X comprises a halogen or $CF_3$; and n is a number from 0 to 10.

2. A polymer according to claim 1, wherein the bifunctional monomer is copolymerized with at least one monofunctional monomer.

3. A polymer according to claim 2, wherein the monofunctional monomer is of formula

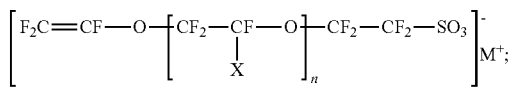

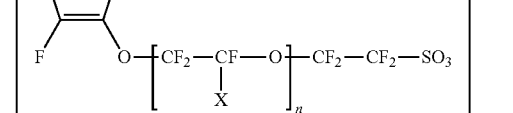

or

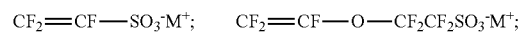

wherein, Y, M+ are as defined in claim 1, and W is a monovalent organic radical alkyl, alkenyl, aryl, arylalkyl, alkylaryl of 1 to 12 carbon atoms unsubstituted or substituted with one or more substituents oxa, aza or thia.

4. A polymer according to claim 2, wherein at least one monofunctional monomer is of formula:

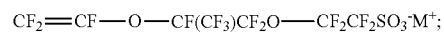

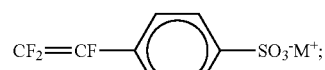

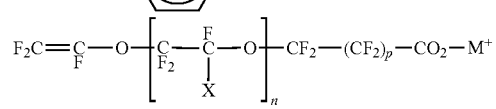

-continued
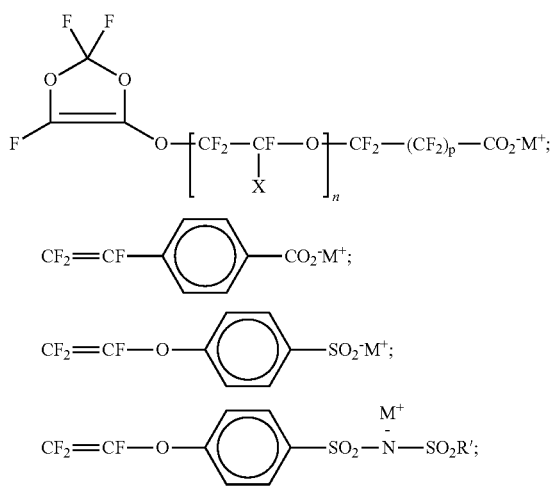
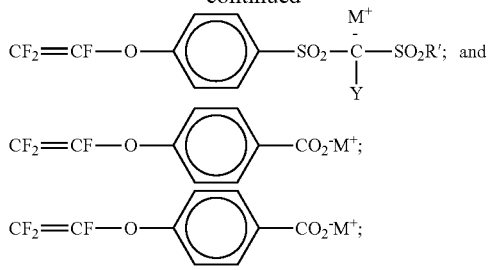
and mixtures thereof, and wherein p=1 or 2; M and n are as defined above, X comprises a halogen or $CF_3$ and R' comprises a monovalent organic radical comprising from 1 to 12 carbon atoms, fluorinated partially, or entirely; or non fluorinated, and unsubstituted or substituted with one or more oxa, aza, thia, or dioxathia; and n is a number from 0 to 10.
* * * * *